US008652360B2

(12) United States Patent
Texier-Nogues et al.

(10) Patent No.: US 8,652,360 B2
(45) Date of Patent: Feb. 18, 2014

(54) SEMICONDUCTOR NANOCRYSTALS

(75) Inventors: Isabelle Texier-Nogues, Grenoble (FR); Aude Bernardin, Grenoble (FR)

(73) Assignee: Commissariat a l'Energie Atomique, Paris (FR)

( * ) Notice: Subject to any disclaimer, the term of this patent is extended or adjusted under 35 U.S.C. 154(b) by 517 days.

(21) Appl. No.: 12/555,022

(22) Filed: Sep. 8, 2009

(65) Prior Publication Data
US 2010/0200813 A1    Aug. 12, 2010

(30) Foreign Application Priority Data
Sep. 8, 2008 (FR) ...................................... 08 56030

(51) Int. Cl.
*H01B 1/00* (2006.01)
*H01B 1/12* (2006.01)
*H01R 4/42* (2006.01)

(52) U.S. Cl.
USPC ................... 252/500; 257/E21.214; 438/758; 549/214; 562/507

(58) Field of Classification Search
USPC ................... 252/500; 257/E21.214; 438/758; 549/214; 562/507
See application file for complete search history.

(56) References Cited

U.S. PATENT DOCUMENTS

2006/0110782 A1   5/2006   Bertozzi et al.
2008/0299046 A1   12/2008  White et al.

FOREIGN PATENT DOCUMENTS

| WO | WO 00/28088 | 5/2000 | |
|----|----|----|----|
| WO | WO 2006/050262 A2 * | 5/2006 | ........... C07K 14/705 |
| WO | WO 2006/115547 A2 | 11/2006 | |
| WO | WO 2007/125429 A2 | 11/2007 | |
| WO | WO 2008/016371 A1 | 2/2008 | |

OTHER PUBLICATIONS

Jyoti K Jaiswal, Ellen R Goldman, Hedi Mattoussi & Sanford M Simon. Use of quantum dots for live cell imaging, Nature Methods, vol. 1 No. 1, Oct. 2004, 73-78.Published in Association With Cold Spring Harbor Laboratory.*
Neeraja Vundyala, et al., "Biotin-functional oligo(p-phenylene vinylene)s synthesized using click chemistry", Elsevier, Tetrahedron Letters, vol. 49, No. 45, XP-002531564, Aug. 28, 2008, pp. 6386-6389.
Ming Li, et al., "Responsive Polymer-Protein Bioconjugates Prepared by RAFT Polymerization and Copper-Catalyzed Azide-Alkyne Click Chemistry", Macromolecular Rapid Communications, vol. 29, No. 12-13, XP-002531190, Jul. 1, 2008, pp. 1172-1176.
Hartmuth C. Kolb, et al., "The growing impact of click chemistry on drug discovery", Drug Discovery Today, Elsevier Science Ltd., vol. 8, No. 24, XP-002377521, Dec. 15, 2003, pp. 1128-1137.

(Continued)

*Primary Examiner* — Bijan Ahvazi
(74) *Attorney, Agent, or Firm* — Oblon, Spivak, McClelland, Maier & Neustadt, L.L.P.

(57) ABSTRACT

The present invention aims to provide a method of use for surface-modifying a semiconductor nanocrystal comprising at least the steps consisting in having a semiconductor nanocrystal, the organic coating layer of which is provided, at the outer surface of the nanocrystal, with at least one reactive group G1 that reacts according to a cycloaddition reaction of click chemistry type; and bringing said nanocrystal together with an adjoining material provided at the surface with at least one G2 group complementary to the G1 group with respect to said click chemistry reaction, under conditions favorable to the interaction of said G1 and G2 groups, characterized in that said G1 and G2 groups are respectively an azide and a strained cycloalkynyl radical, or vice versa.

10 Claims, 2 Drawing Sheets

(56) References Cited

OTHER PUBLICATIONS

Julian A. Codelli, et al., "Second-Generation Difluorinated Cyclooctynes for Copper-Free Click Chemistry", Journal of the American Chemical Society, vol. 130, No. 34, XP-002531600, Aug. 5, 2008, pp. 11486-11493.

Rajesh Ranjan, et al., "Combination of Living Radical Polymerization and Click Chemistry for Surface Modification", Macromolecules, American Chemical Society, vol. 40, No. 17, XP-002531189, Jul. 24, 2007, pp. 6217-6223.

* cited by examiner

SEMICONDUCTOR NANOCRYSTALS

The field of the invention is that of semiconductor nanocrystals, especially fluorescent semiconductor nanocrystals also known as quantum dots.

The present invention mainly aims to provide a novel method that can be used for the grafting, in particular of organic molecules, polymeric biomolecules, dendrimers, metal complexes or else proteins, enzymes, nucleic acids, lipids and antibodies at the surface of these nanocrystals.

Semiconductor nanocrystals are particles that are very interesting with respect to the properties conferred by their semiconductor core.

They are simultaneously endowed with an intense fluorescence and a slow rate of photobleaching. They allow an adjustment of their emission wavelength via their size and/or the composition of their semiconductor core. They have a broad excitation band which makes it possible to simultaneously excite several nanocrystals at the same wavelength (facilitated multiplexing).

These properties, which give them significant advantages relative to organic fluorophores, are taken advantage of in very diverse applications.

Thus, semiconductor nanocrystals are used for their optical and/or electronic (redox, and/or electric conduction) properties for the manufacture of sensors, photovoltaic cells, etc.

Furthermore, they are widely used in the field of biology, in particular as markers in imaging, especially optical imaging, or as phototherapy agents.

Semiconductor nanocrystals are generally synthesized in an organic solvent medium where they are in a form stabilized by ligands, generally phosphines, phosphine oxides, or fatty chains bearing, at their end, an amine, carboxylic acid or thiol functional group. These stabilizing ligands make it possible to control the growth of the nanoparticles during their synthesis.

However, the nanocrystals obtained at the end of these conventional syntheses do not prove to be usable as they are for numerous applications.

Thus, for biological applications, it is desirable to give these naturally water-insoluble nanocrystals a solubility in an aqueous medium.

Furthermore, depending on the applications in question, it may be necessary to couple them to organic molecules, metal complexes, biomolecules, etc. and therefore to have nanocrystals bearing reactive functional groups that are favourable for producing these couplings.

Two main functionalization methods are currently used for attaining nanocrystals that conform to one and/or the other of the two aforementioned requirements.

The first functionalization method relies on an exchange with stabilizing ligands, that is to say organic chelating ligands used during the synthesis of nanocrystals in an organic solvent. These stabilizing ligands are replaced by bifunctional organic chelating ligands, that comprise, on the one hand, a chemical group that has a strong affinity for the surface of the nanocrystals and, on the other hand, a chemical group that favours a good solubility of the nanocrystals, in water or in an aqueous buffer, and which can be functionalized by a molecule of interest.

These substituting organic chelating ligands may be, for example, thiols, carboxylate anions (derived from fatty acids in particular), phosphates, phosphonates, phosphines, amines, carbodithioates, such as mercaptoacetic acid, oleic acid, poly(ethylene glycol) chains functionalized at their end(s) by these same groups. It is also possible to use ligands that have two or more of these same groups in order to further promote, via an entropic effect, the interaction between the ligand and the nanoparticle, like, for example, dihydrolipoic acid (2 thiol functional groups) and phosphines in the form of oligomers. According to one embodiment variant, this first layer of bifunctional organic ligands thus formed may be protected by grafting thereto, in a covalent manner, an organic polymer onto which the molecules of interest will in fine be grafted.

The second functionalization method itself uses amphiphilic polymers or molecules. The hydrophobic part of the ligand or of the polymer interacts with the hydrophobic part of the stabilizing ligands of nanocrystal origin, and the hydrophilic part serves to stabilize said nanocrystals in an aqueous buffer.

The hydrophobic part may be, for example, composed of one or more hydrocarbon-based chains, or of aromatic rings.

Such amphiphilic polymers or ligands may be, for example:
  amphiphilic molecules, such as for example fatty acids, fatty ($C_6$ and above) chains functionalized by hydrophilic groups, such as for example amine, phosphate, sulphate, etc.;
  amphiphilic organic polymers; and
  phospholipids such as, for example, phosphatidylethanolamine (PE), phosphatidylcholine (PC) or polymers such as PEG-PE/PC (PEG=poly(ethylene glycol), PEG-PE=PE functionalized by a PEG chain), capable of self-assembling into a micelle.

These two functionalization methods, suitable for forming an aqueous solubilisation layer at the surface of the nanocrystals, therefore respectively have the additional advantage of allowing the introduction of reactive functional groups (essentially amines, thiols and carboxylic acids, for commercial nanocrystals) that are favourable to the subsequent grafting of the nanocrystal in question with an adjoining material (proteins, enzymes, nucleic acids, lipids, antibodies, oligosaccharides, metal complexes, conductive polymers or polymers for non-linear optics, surfaces, silica beads, photovoltaic cells, etc.).

The conventional methods of grafting used on semiconductor nanocrystals that take advantage of the reactive functional groups present on the surface of their solubilisation layer are mainly the following:
  coupling between activated carboxylic acids (often in NHS-activated form) and amines;
  coupling between thiols and maleimides; and
  coupling between carbonyls and oxyamines.

These methods make it possible to conjugate inter alia proteins, nucleic acids, antibodies, oligosaccharides, metal complexes, to the semiconductor nanocrystals for various applications.

Unfortunately, this functionalization method is not always satisfactory. Specifically, depending on the structure of the grafted molecules, it is possible to jointly produce undesirable reactions with the amines/thiols/carboxylic acids present.

In order to make up for this drawback, cycloaddition reactions known as click chemistry between azides and alkynes have recently been successfully applied to the functionalization of nanocrystals (1).

Thus, Binder et al. give an account of a functionalization of semiconductor nanocrystals that relies on the exchange of stabilizing ligands originating from these nanocrystals with phosphines, bearing either terminal alkynes or azides, for the purpose of consecutively carrying out 1,3-dipolar cycloadditions. These cycloadditions are carried out either via a thermal route (95° C.) in toluene or by click chemistry in THF, in the presence of a base, a ligand and Cu(I). The expected cycloaddition products are obtained in both cases, and the formation of triazoles is proven by infrared monitoring of the disappearance of the characteristic band for azides at 2100 cm$^{-1}$.

Unfortunately, the semiconductor nanocrystals obtained by click chemistry lose almost all their fluorescent property. The explanation proposed is a quenching due to the residual presence of Cu(I) ions. The use of conventional click chemistry (that is to say which is catalyzed with Cu(I)) for the modification of quantum dots does not therefore make it possible to retain the innate fluorescent properties.

For the purpose of overcoming this drawback, it has been proposed to avoid the presence of copper by activating the alkynes via electron-withdrawing groups. However, these compounds are then capable of undergoing Michael reactions and therefore of leading to the formation of products other than those that are expected.

Therefore, there remains a need for a simple and selective method for achieving the grafting of material to the outer surface of semiconductor nanocrystals without significantly affecting their photoluminescent, and more particularly fluorescent, power.

The present invention specifically aims to provide a novel process for functionalizing semiconductor nanocrystals in accordance with these requirements.

Thus, according to one of its aspects, the present invention relates to a method for surface-modifying a semiconductor nanocrystal comprising at least the steps consisting in:

having a semiconductor nanocrystal, the organic coating layer of which is provided, at the outer surface of the nanocrystal, with at least one reactive group G1 that reacts according to a cycloaddition reaction of click chemistry type; and bringing said nanocrystal together with an adjoining material provided at the surface with at least one G2 group complementary to the G1 group with respect to said click chemistry reaction, under conditions favourable to the interaction of said G1 and G2 groups, characterized in that said G1 and G2 groups are respectively an azide and a strained cycloalkynyl radical, or vice versa.

In the meaning of the present invention, the expression "said G1 and G2 groups are respectively an azide and a strained cycloalkynyl radical, or vice versa" means that the G1 group is an azide and the G2 group a strained cycloalkynyl radical or that the G1 group is a strained cycloalkynyl radical and the G2 group an azide.

According to another of its aspects, the invention relates to a semiconductor nanocrystal, in particular that is fluorescent, the organic coating layer of which is provided, on the outer surface of the nanocrystal, with at least one strained cycloalkynyl radical that is reactive with regard to an azide according to a cycloaddition reaction of click chemistry type.

According to yet another of its aspects, the present invention targets a semiconductor nanocrystal, in particular that is fluorescent, the organic coating layer of which is surface-grafted to at least one material, especially a substrate and/or at least one molecule of interest, obtained according to the process of the invention.

Such a substrate may especially be chosen from surfaces of the following types: metallic (gold, silver, platinum, etc.), semiconductor (silicon, germanium, etc.), oxide (alumina, $SiO_2$, $TiO_2$, etc.), or organic such as for example plastics, polymers or gels.

The inventors have thus observed that the choice of a strained cycloalkynyl as a group that is complementary to an azide for the purposes of modifying fluorescent semiconductor nanocrystals via a reaction of click chemistry type makes it possible to satisfy all the aforementioned requirements.

Indeed, it is known that azides react very rapidly in the presence of strained double bonds in cyclic compounds. In particular, document WO 2006/050262 takes advantage of this acceleration of the reaction due to the ring strain in order to carry out a cycloaddition between azide and cyclooctyne for the purposes of chemical modifications of cells in a living organism.

However, to the knowledge of the inventors, this cycloaddition of click chemistry type of an azide to a strained cycloalkyne has never been taken advantage of for the surface modification of fluorescent nanocrystals. Similarly, the functionalization of the organic coating layer at the surface of nanocrystals with at least one strained cycloalkynyl radical has never been considered in order to make it possible to obtain, simply and under mild conditions, fluorescent nanocrystals that are surface-grafted either to a substrate or to a molecule of interest, and which nevertheless remain endowed with a satisfactory fluorescence.

The process that is the subject of the invention proves advantageous in several ways.

Firstly, it allows the conjugation of molecules of interest, or of biomolecules, to the surface of semiconductor, in particular fluorescent, nanocrystals under mild and biocompatible conditions.

The absence of base makes it possible to maintain a pH which ensures the stability of the nanocrystals in the aqueous phase.

The absence of copper(I) makes it possible to avoid the phenomenon of extinction of the fluorescence of fluorescent semiconductor nanocrystals.

It is no longer necessary to add additives, such as polytriazoles which allow a self-catalysis of the reaction by stabilizing the copper(I).

Finally, the functionalization may be carried out in an aqueous medium and at ambient temperature, i.e. conditions that are particularly valued from an industrial point of view, and moreover which therefore prove compatible with the grafting of sensitive molecules of interest, such as nucleic acids and certain proteins.

Other features and advantages of the invention will emerge more clearly from the description that follows.

Semiconductor Nanocrystals

Nanocrystals may be defined as "nanoscale" crystalline objects, that is to say that their size is generally less than 150 Å and preferably is within the range of 12 to 150 Å.

The nanocrystals considered in the invention are inorganic nanocrystals with an organic coating layer.

The size of the inorganic crystalline core is generally less than 100 nm, and preferably between 1 and 25 nm.

The semiconductor nanocrystals are generally composed of at least one metal, one metal oxide and/or at least one semiconductor compound.

The nanocrystals are, for example, composed of at least one metal.

The metal may be any metal, but it is generally chosen from transition metals, rare-earth metals, metals from groups IIIA, IVA and VA from the Periodic Table of the Elements, and alloys thereof, and mixtures of these metals and alloys.

Preferably, the metal is chosen from aluminium, copper, silver, gold, indium, iron, platinum, nickel, molybdenum, titanium, tungsten, antimony, palladium, zinc, tin, alloys thereof, and mixtures of these metals and alloys.

Preferably the metal is gold.

The nanocrystals may also be composed of at least one metal oxide, such as for example an oxide of iron, titanium, aluminium, platinum, gadolinium or hafnium. Preferably, the nanocrystals are iron oxides, including in particular magnetite and maghemite, gadolinium oxide or hafnium oxide.

The nanocrystals may be composed of at least one semiconductor compound. The semiconductor compound may be a semiconductor of formula AB in which A represents a metal or a metalloid in the +II oxidation state and B represents an element in the −II oxidation state.

A is generally chosen from Mg, Ca, Sr, Ba, Zn, Cd, Hg, Sn, Pb and mixtures of these, and B is generally chosen from O, S, Se, Te and mixtures of these.

Examples of A(II)B(VI) compounds are MgS, MgSe, MgTe, CaS, CaSe, CaTe, SrS, SrSe, SrTe, BaS, BaSe, BaTe, ZnO, ZnS, ZnSe, ZnTe, CdS, CdSe, CdTe, HgS, HgSe, HgTe, SnS, SnSe, SnTe, PbS, PbSe, PbTe and mixtures of these.

The semiconductor compound may also be a semiconductor of formula CD (C(III)D(V)) in which C represents a metal or a metalloid in the +III oxidation state and D represents an element in the −III oxidation state.

C is generally chosen from Ga, In, and mixtures thereof, and D is generally chosen from Sb, As, P, N and mixtures thereof.

Examples of these C(III)D(V) semiconductor compounds are GaAs, GaSb, GaN, InGaAs, InN, InGaN, InP, InAs, InSb and mixtures thereof.

It is also possible to use semiconductor compounds from group IV such as silicon or germanium.

It is also possible to use a mixture of AB, CD compounds and of semiconductors from group IV.

In one embodiment of the invention, the semiconductor nanocrystal has a core/shell(s) structure, said core being composed of a nanocrystal as described above that is composed of at least one metal and/or at least one semiconductor compound whilst the shell(s) is (are) each composed of a layer of a metal and/or of at least one semiconductor compound comprising at least one metal.

This core has, for example, a diameter of 10 to 250 Å whilst the shell(s) has (have) a thickness of 3 to 30 Å. When the nanocrystal does not comprise shell(s), it generally has a diameter of 15 to 150 Å.

The organic coating layer generally has a thickness of 5 to 100 Å.

All combinations are possible for the materials that form the core, on the one hand, and the shell(s) on the other hand, but preferably the core is made from a first semiconductor compound, whilst the shell surrounding said core (in the case of a single shell) or the first shell containing the core in the case where the core is surrounded by several shells, is made from a second semiconductor compound that is different from the first semiconductor compound (that forms the core).

The first and second semiconductor compounds are chosen from the semiconductor compounds already described above.

Preferably, the core is made from a first semiconductor compound of A(II)B(VI) type described above, such as CdSe or a C(III) D(V) compound described above such as InP, whilst the shell surrounding the core or the first shell surrounding the core is made from a second semiconductor compound of A(II)B(VI) type that is different from the first semiconductor compound chosen, for example, from ZnSe, ZnS and CdS.

In the case of multiple shells, two successive shells are generally made from different semiconductor compounds.

Thus, in the case of multiple shells, the materials forming the shells may be chosen from all the possible combinations of compounds cited previously, for example these compounds may be chosen from ZnSe, CdS and ZnS. For example, it will be possible to have a first shell made of ZnSe or of CdS and a second shell made of ZnS.

As specified previously, the nanocrystals considered in the invention have an organic coating layer of specific solubilisation.

Organic Coating Layer

The semiconductor nanocrystals considered in the invention have an organic coating layer that is modified since it is provided, at the outer surface of the nanocrystal, with at least one reactive group G1 that reacts according to a click chemistry reaction.

More specifically, this layer comprises at least one specific ligand corresponding to the general formula (I):

L-X-E-A-G         (I)

in which:

L is a chelating ligand, in particular which may be chosen from the group consisting of phosphine, phosphine oxides, or fatty chains bearing, at their end, an amine, carboxylic acid, or thiol functional group, a 1,1-dithiolate (—C(S)S$^-$) group or a 1,1-diselenoate (—C(Se)Se$^-$) group;

E is an organic spacer group which may allow a charge transfer or else may be insulating;

X is the reaction product of one reactive functional group present on the chelating ligand L and a complementary reactive functional group present on the organic spacer group E such as, for example, thiol/maleimide, amine/activated carboxylic acid or carbonyl/oxyamine;

A represents a single bond or a group chosen from the group consisting of —CONH, —NHCO—, —OCH$_2$CONH—, —NHCOCH$_2$O—, —O—, —S—; and G is a strained cycloalkynyl or azide radical.

Within the meaning of the present invention, the expression "strained cycloalkynyl" extends to the heterocycloalkynyls. More particularly, it is a ring having 7, 8 or 9 ring members.

According to one preferred mode of the invention, the cycloalkynyl group is a cyclooctynyl group.

The strain applied to the cycloalkynyl group may be increased in various ways, for example by the use of heteroatoms, the degree of unsaturation, or the deformation due to torsion, the use of electron-withdrawing groups, etc. The corresponding derivatives are also covered under the expression "strained cycloalkynyl".

Thus, the strained cycloalkynyl according to the invention may be a compound in which one or more carbon atom(s) of the cycloalkynyl ring, apart from the two carbon atoms joined by a triple bond, is substituted by one or more electron-withdrawing group(s), for example a halo (bromo, chloro, fluoro, iodo) or nitro group, a cyano group or a sulphone group. When the electron-withdrawing group is a nitro, cyano or sulphone group, the electron-withdrawing group is not directly bonded to the cycloalkynyl ring.

As another group capable of being present on the cycloalkynyl, mention may be made, non-exhaustively, of carboxyl, amine (for example alkylamine (for example lower alkylamine), arylamine), ester (for example alkyl ester (for example lower alkyl ester, benzyl ester), aryl ester, substituted aryl ester), thioester, sulphonyl halide, alcohol, thiol, succinimidyl ester, isothiocyanate, iodoacetamide, maleimide or hydrazine groups, etc.

According to one preferred variant, E corresponds to the following formula:

—R$_1$—R—         (II)

where $R_1$ represents:
a single bond;
a

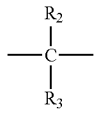

group
where $R_2$ and $R_3$ independently represent a hydrogen, an alkyl radical, an aryl radical, an alkoxy radical, a halogen;
a

group
where R' represents a hydrogen, an alkyl radical, an aryl radical, an alkoxy radical, a halogen;
a

group
where R' has the meaning already given above;
a

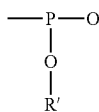

group
where R' has the meaning already given above;
—O—;
—S—;
—Se—;
and R represents a linear or branched alkylene group having from 1 to 30, preferably from 1 to 8, carbon atoms; one or more carbon atoms of said alkylene group optionally being replaced by one or more heteroatoms chosen from O, N, S, P and Si; said alkylene group optionally comprising, in addition, one or more double and/or triple bonds such as carbon-carbon double and/or triple bonds; and said alkylene group optionally being, in addition, substituted by one or more groups chosen from halogens, such as chlorine, bromine, iodine and fluorine, heterocycles, aryl, hydroxyl, alkoxy, amino, acryl, carboxamido, =O, —CHO, —CO$_2$H, —SO$_3$H, —PO$_3$H$_2$, —PO$_4$H$_2$, —NHSO$_3$H, sulphonamide, monoalkylamino, or trialkylammonium radicals, or else by a dialkylamino radical in which the two alkyl groups may form, together with the nitrogen atom of said dialkyl ($C_1$-$C_4$) amino group to which they are bonded, a ring which may be interrupted by one or more nitrogen, oxygen or sulphur atoms, and Z groups; or R represents a heterocycle, an aryl radical, an aryl radical fused to one or more other aryl rings and/or alkyl rings or heterocycles, a cycloalkyl radical, a cycloalkyl-alkyl radical, an alkyl-cycloalkyl radical, an arylalkyl radical, an alkylaryl radical, a heterocycloalkyl radical or an alkyl-heterocycloalkyl radical.

The E group may advantageously be a polyethylene glycol (PEG) chain that makes it possible to improve the solubility of the compound, or any other polymer, dendrimers, oligomers or hydrogels that make it possible, for example, to encapsulate fluorescent semiconductor nanocrystals in materials, gels or a formulation (plastics for optics and electronics, dispensing phototherapy agents, for example).

The E group may also be a small organic molecule that makes it possible to provide the complementary reactive function, for example ethylene diamine, glycolic acid, cysteamine, or any other organic molecule that makes it possible to provide acids/amines/thiols.

The E group may be a hydrocarbon-based group comprising one or more unsaturated groups, for example of alkenic type. An example of such a group may be an alkylene group as defined above interrupted by one or more alkenically unsaturated groups. When the E group comprises at least two unsaturated groups, it may give the compounds an ability to be crosslinked.

The E group may also be a hydrocarbon-based group comprising one or more aromatic groups. Mention may be made, for example, of a group comprising aromatic groups fused with unsaturated linear groups, such as a group that results from the linking of a phenylene-vinylene unit. These groups help to confer non-linear optical properties.

Mention may also be made of a group comprising pyrrol and/or thiophene units. These groups help to give the material electronic conduction properties. Mention may be made, for example, of a group comprising one or more aromatics substituted by one or more aromatic groups, such as a group comprising a linkage of quinone units or of diazo units. These groups help to give the compound possessing them photo/electroluminescence properties.

Obtaining the preceding nanocrystals that are intended to be used in the first step of the process according to the invention clearly comes under the competences of a person skilled in the art.

According to a first production variant, nanocrystals already provided at the surface with a layer of chelating ligands but that are not in accordance with the invention are brought together, generally in solution, with ligand compounds that are already functionalized with at least one azide or strained cycloalkynyl radical and the whole assembly is kept in contact for a satisfactory duration in order to produce, at the surface of the nanocrystals, an at least partial exchange of the original chelating ligands with the ligand compounds functionalized with at least one azide or strained cycloalkynyl radical.

According to a second variant, it is possible to proceed directly to the functionalization of the chelating ligands forming the outer layer of the nanocrystals with strained cycloalkyne or azide units.

The materials comprising an azide suitable for the present invention, along with the methods for preparing materials that comprise the azide suitable for the present invention, are also well known to a person skilled in the art.

Method

The present invention therefore provides a method that can be used to surface-modify nanocrystals via a [3+2] cycloaddition reaction of click chemistry type between an azide moiety and a strained cycloalkynyl moiety, one of these two moieties, preferably the strained cycloalkynyl, being present on the outer surface of the organic coating layer of the nanocrystals to be grafted and the other being bonded to an adjoining material intended to be attached to the surface of the nanocrystals.

As it emerges from the aforegoing, the invention takes advantage of the large bond angle deformation of the acetylene group in the strained cycloalkynyl group, which provides the ring strain. This destabilization of the ground state versus the transitional state gives the reaction a very high acceleration compared to unstrained alkynes.

The azide group and the strained cycloalkynyl group borne respectively by each of the materials present, namely the nanocrystal or the adjoining material, interact to form a final conjugate product comprising a fused azide/cycloalkyne ring.

The reaction is advantageously obtained without a catalyst.

It may advantageously be carried out at ambient temperature and in an aqueous medium. The activation energy needed for the reaction is provided by the azide group and the strained cycloalkynyl group.

The method according to the invention may comprise, at the end of its second step, a supplementary step during which the nanocrystals provided with an organic coating layer modified according to the invention (I) (said nanocrystals having been optionally precipitated, separated, washed, then dried) are subjected to an irradiation with a light, preferably an ultraviolet (UV) light.

In other words, the nanocrystals are subjected to an exposure to light, preferably ultraviolet light, for a given period, generally from one or a few minutes to one or a few hours, for example from one minute to 10 hours.

This irradiation or exposure leads to a photochemical method that improves the effectiveness of the photoluminescence.

Surface-Grafting of the Nanocrystals

Within the meaning of the present invention, the term "grafting" covers the following two reactions, namely:
- the term "anchoring" which refers to the immobilization of a compound, in this case a nanocrystal, on the surface of a substrate; and
- the term "coupling" which describes the reaction between at least one terminal functional group of a first compound, in particular a nanocrystal, and at least one complementary functional group, borne by a second compound, in particular a molecule of interest.

According to one embodiment variant, the method according to the invention is carried out for the purposes of anchoring nanocrystals to the surface of a material of substrate type.

For example, a solid or semi-solid support, in particular a support suitable for use as a nucleic acid (DNA, RNA, oligonucleotide) chip, a protein chip, a sugar chip, a cell chip or as a photosensitizer for photovoltaic cells, or as an optical marker for silica beads (for chips in suspension).

The method according to the invention generally comprises bringing an azide group present on the substrate together with a strained cycloalkynyl group present on the nanocrystal.

According to another embodiment variant, the method according to the invention is carried out in order to couple the outer surface of the semiconductor nanocrystals with one or more molecules of interest.

As an example of molecules of interest, mention may also be made of markers, dyes, fluorophores, (coumarins, fluorescein, modified fluoresceins, rhodamines, guanines, borondipyrromethene, oxadines and others), toxins (including cytotoxins), linkers, therapeutic, cosmetic and phytosanitary active agents, members of a specific binding pair, peptides, amino acids and amino acid residues, polypeptides (including peptides and proteins), sugars and sugar residues, photosensitizors such as, for example, eosin, rose bengal, phthalocyanines, chlorins, bacteriochlorins, porphyrins such as for example tetrakis[meso(4-ethynylphenyl)]porphyrin, 1,10-(4-ethynylphenyl)-5,15-(4-mesityl)porphyrin and 1-(4-ethynylphenyl)-5,10,15-(4-mesityl)porphyrin, the presence of which on a surface is particularly useful in the field of molecular electronics and phototherapy; compounds having a cis-trans isomerism such as derivatives of diarylethylenes, of spiropyrans, of spiroxazines, of fulgides or of azobenzene, the presence of which on a surface is particularly useful for the manufacture of photocontrolled molecular switches.

The molecules of interest may be of natural origin, or produced in a synthetic or recombinant manner, and may be isolated, purified, or else present in the native medium of the unmodified molecule on which the target molecule that generally comprises an azide is based, for example at the surface or inside a cell.

When the target molecule is a polypeptide, the polypeptide may be composed of D, L, or both D and L amino acids, and may also be modified, whether in a natural, synthetic or recombinant manner, in order to include other groups therein. For example, the target polypeptide may be a lipoprotein, a glycoprotein or any other modified protein.

The methods and nanocrystals according to the invention have multiple applications, be it in research or in diagnostics.

The research applications also include drug discovery or screening applications: like any contrast agent, the invention allows the visualization of molecules of interest (receptor, glucose, antigen, etc.) or of biological mechanisms (endocytosis, neoangiogenesis, apoptosis, enzyme activities, etc.) and therefore makes it possible to identify therapeutic targets.

It also makes it possible to monitor the effect of a medicinal treatment (for example a cytotoxic, enzyme inhibitor, etc. treatment) or the detection of tumours (by means of specific markers).

As other applications of interest, mention may be made of the study of the functional and physical characteristics of a receptor, proteomics, metabolomics, etc.

BIBLIOGRAPHICAL REFERENCES (1) Binder, W. H.; Sachsenhofer, R.; Straif, C. J.; Zirbs, R., *Journal of Materials Chemistry* 2007, 17, (20), 2125-2132

The following examples and figures are presented by way of illustration and without limitation in the field of the invention.

EXAMPLES

Example 1

Figure 1:
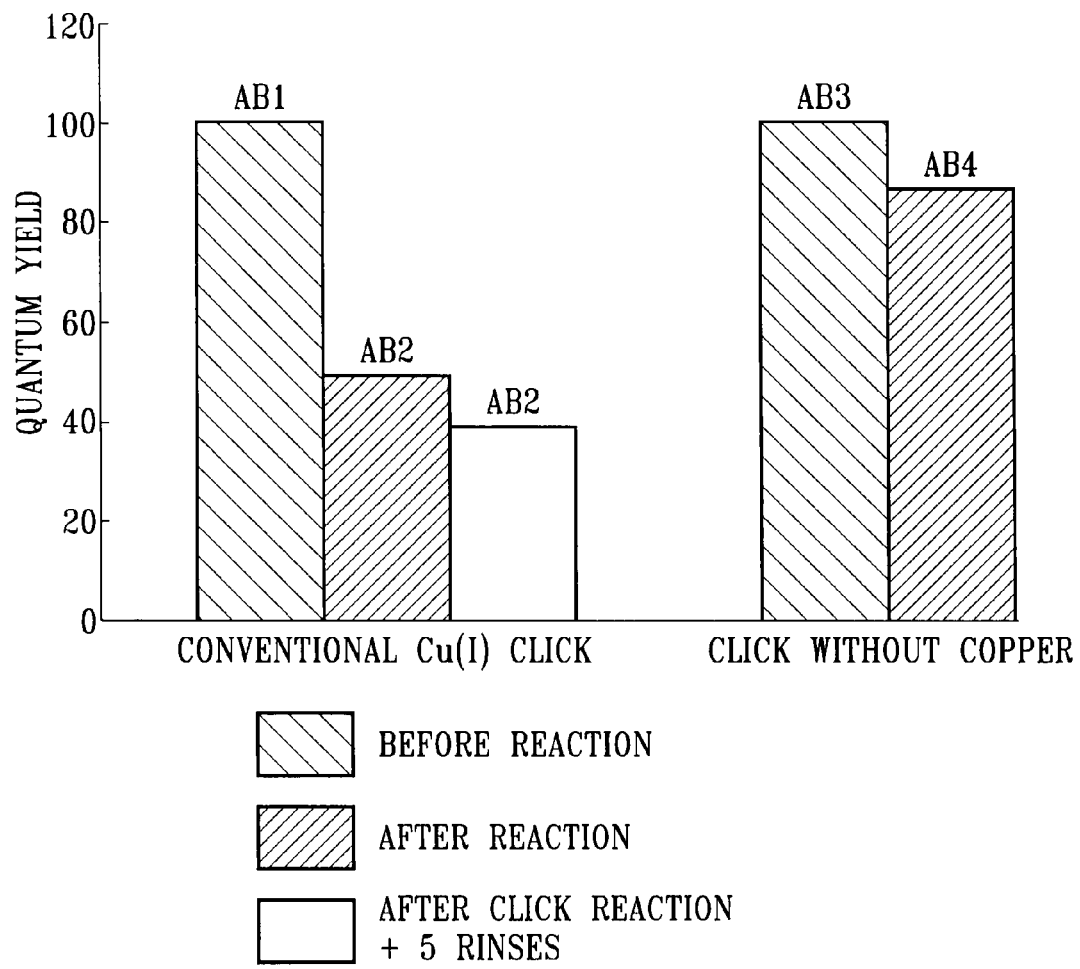
FIG. 1: It gives an account of the quantum yields of the QDots modified by click chemistry considered in Example 2.

Synthesis and Characterizations of a Fluorescent Nanocrystal Modified by a Cyclooctynyl Unit 1. Synthesis of Cyclooctyne a) Synthesis of 8,8-dibromobicyclo[5.1.0]octane Introduced into a dry round-bottomed flask that is under argon are 3.65 g of cycloheptene (i.e. 38 mmol), then 8.52 g of t-BuOK (i.e. 76 mmol, 2 eq.) and 9 ml of previously distilled pentane. The creamy yellow solution is stirred vigorously and placed in an ice/salt bath. Then 4.9 ml of bromoform (i.e. 57 mmol, 1.5 eq.) are added dropwise. During the first additions, a relatively violent gaseous release is observed, then as the addition progresses the solution becomes brown ochre. During addition, around 5 ml of pentane are added to allow correct stirring of the solution. Once the addition is finished, the mixture is left to come to room temperature overnight, under argon and with vigorous stirring.

Around 50 ml of water are then added and the pH is neutralized with 1M HCl. The organic and aqueous phases are separated; the aqueous phase is extracted with 3×20 ml of pentane and the pentane phase is washed with 3×20 ml of water. The organic phase is then dried over MgSO$_4$ and the solvent evaporated under vacuum. An orangey yellow oil is obtained with a mass m=10.814 g.

The product is then purified by a simple filtration over silica with 5% cyclohexane/AcOEt as eluant. A colourless oil having a total mass of 9.100 g is obtained after purification, i.e. with a yield of 90%.

b) Synthesis of methyl 2-bromocyclooctene-3-glycolate

Added to a solution of 8,8-dibromobicyclo[5.1.0]octane (2.5 g i.e. 9.3 mmol) and methyl glycolate (6.35 ml, i.e. 83.9 mmol) dissolved in 5 ml of anhydrous toluene in a dry round-bottomed flask, under Ar and protected from the light by aluminium foil, are 3.85 g of silver perchlorate (i.e. 18.6 mmol). The reaction is stirred for 1 h 30 min at room temperature, then the silver salts are filtered over a frit and washed with AcOEt. The solution is concentrated under vacuum to give a viscous brown oil which is purified by silica gel chromatography (2-15% AcOEt in cyclohexane) to obtain the product in the form of a yellow oil having a mass m=1.6 g, i.e. 65% yield.

c) Synthesis of cyclooct-1-yn-3-glycolic acid

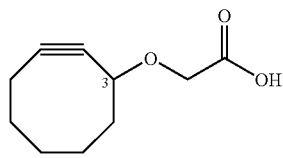 [SMILES: O=C(O)COC1C#CCCCCC1]

Added to 250 mg of methyl 2-bromocyclooctene-3-glycolate (i.e. 0.90 mmol) is a solution of sodium methylate at a concentration of 0.5M in methanol. The mixture is stirred for 2 days at room temperature.

The reaction is acidified with 1M HCl, then extracted with AcOEt, dried over MgSO$_4$ and the solvents are evaporated. The product is purified over silica gel with AcOEt and is obtained in the form of a yellow oil having a mass of 120 mg, i.e. 80% yield.

$^1$H NMR (CDCl$_3$, 200 MHz): δ (ppm) 1.3-2.3 (m, 10H); 4.45 (d, J$_{9\text{-}9'}$=17 Hz, 1H, H$_9$); 4.50 (m, 1H, H$_3$); 4.58 (d, J$_{9\text{-}9'}$=17 Hz, 1H, H$_{9'}$);

$^{13}$C NMR (CDCl$_3$, 50 MHz): δ (ppm)

Mass: ESI m/z

2. Synthesis of the AminoPEG-Cyclooctyne Modified Nanocrystal

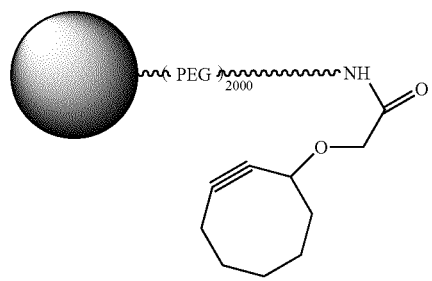

The starting nanocrystal is the quantum dot sold by Invitrogen under the name QDots ITK545.

Before reaction, the QDots ITK 545 are transferred from the storage borate buffer into PBS (phosphate-buffered saline, 0.01M with 0.154M of NaCl at pH 7.4)

In order to do this 75 µl of the 8 µM solution are filtered over Microcon® filters for 5 min at 5000 g (by centrifugation), then rinsed with the same volume of PBS by centrifugation for 5 min at 3000 g, and resuspended in 75 µl of PBS (1000 g for 3 min, filter turned over).

0.5 mg of EDC(N-(3-dimethylaminopropyl)-N'-ethylcarbodiimide) and 10 µl of a solution of cyclooctyne in DMSO (0.11 mg, i.e. 10 equivalents per function, 100 functions per nanoparticle) are added to the 75 µl of PBS containing the QDots ITK545. The whole mixture is stirred at room temperature, protected from the light, for 5 h.

The product is then purified over a size exclusion column GL25 (Healthcare GE), previously equilibrated with PBS. The product is recovered as a fraction which is then concentrated over Microcon® filters at 3000 g for 5 min, and resuspended in 75 µM of PBS at 1000 g for 3 min.

An electrophoresis carried out on 1% agarose gel, in a TBE buffer at pH 8.3 (deposition of 10 µl of a solution diluted to 10$^{th}$), for 20 min at 100 V makes it possible to highlight the modification of the surface of the nanocrystals; specifically, the compound modified by cyclooctyne groups migrates differently in comparison with the starting product.

Likewise, absorption spectra recorded at 488 nm on a CARY 300 Scan spectrophotometer by Varian, and fluorescence spectra recorded at 488 nm on an LS50B spectrophotometer by Perkin Elmer show that the optical properties of the QDots are not modified by the coupling of cyclooctyne groups at the surface.

The quantum yield is 108% relative to the starting product, measured in PBS.

Example 2

Comparison of the Grafting of a Sugar to QDots-Linear Alkynes and QDots-Cyclooctynes Prepared According to Example 1

1. Synthesis And Characterization of QDots-Linear Alkynes

Before the reaction, the QDots ITK 525 aminoPEG from Invitrogen are transferred from the storage borate buffer into PBS: in order to do that, 60 µl of 8 µM solution are filtered over Microcon® filters for 5 min at 5000 g (by centrifugation), then rinsed with the same volume of PBS by centrifugation for 5 min at 3000 g, and resuspended in 60 µl of PBS (1000 g for 3 min, filter turned over).

0.5 mg of EDC and 5 µl of a solution of undecynoic acid in DMSO (0.087 mg i.e. 10 equivalents per function, 100 functions per nanoparticle) are added thereto. The whole mixture is stirred at RT, protected from the light, for 1 h. Then the product is purified over a G25 size exclusion column (Healthcare GE), previously equilibrated with PBS. The product is recovered as a fraction that is then concentrated over Microcon® filters at 3000 g for 5 min, and resuspended in 60 µM of PBS at 1000 g for 3 min.

The QDots were characterized by gel electrophoresis and their optical properties were determined according to the protocol described in Example 1.

2. Comparison of the Grafting of a Sugar to QDots-Linear Alkynes and QDots-Cyclooctynes The coupling of a sugar bearing an azide was carried out at the same time on the QDots-linear alkynes and on the QDots-cyclooctynes synthesised according to the following two respective reaction schemes.

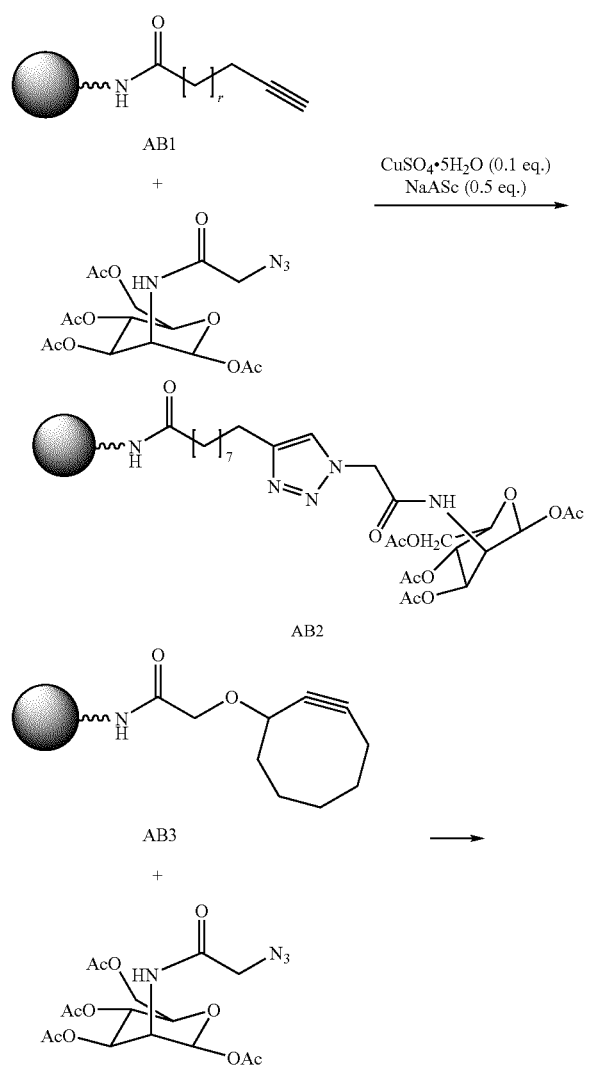

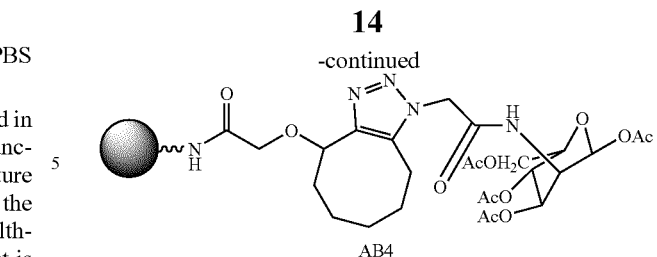

Conventional Click Coupling Between QD-Linear Alkynes and Ac$_4$ManNAz:

Added to a solution of 20 µL of QDots in PBS are 5 µl of a solution of Ac$_4$ManNAz in DMSO (10 eq. per reactive function) and 2 µl of a 1 mM CuSO$_4$/5 mM sodium ascorbate (0.1 eq.) solution. The whole mixture is stirred at ambient temperature for 3 h, then the QDs are purified over Microcon filters by rinsing with PBS (1 rinse or 5 rinses) at 3000 g for 3 minutes. The Qdots are then characterized by gel electrophoresis and their optical properties are determined.

Coupling Between QD-Cyclooctyne and Ac$_4$ManNAz:

Added to a solution of QDots in PBS (20 µl) is a solution of Ac$_4$ManNAz in DMSO (5 µl, 10 eq. per reactive function). Then the whole mixture is stirred at ambient temperature for 3 h; then the QDs are purified over Microcon filters by rinsing with PBS (1 rinse) at 3000 g for 3 minutes. The Qdots obtained are then characterized by gel electrophoresis and their optical properties are determined.

The coupling products obtained are characterized in terms of fluorescent spectrum according to the protocol described in Example 1, and it clearly appears that the quantum yield of the QDots-linear alkynes is very greatly reduced, whereas that of the modified QDots-cyclooctynes remains high relative to the starting product.

FIG. 1 gives an account of the quantum yields of the QDots modified by click chemistry.

Furthermore, the quenching due to the presence of Cu(I) is irreversible: even after several cycles of filtration over Microcon® filter/rinsing with PBS, the quantum yield of the product AB2 does not return to the level of that of the starting product (the latter even decreases due to the fact of this treatment).

Example 3

Functionalization of Glass Slides

The Qdots-cyclooctynes synthesized as described in Example 1 are used to carry out a cycloaddition reaction on the surface of azide-functionalized glass.

Drops of the solution of starting QDots and of QDot-cyclooctynes are incubated at ambient temperature in PBS for 1 h, then the slides are rinsed and the slides observed with a GeneTacIV scanner under excitation at 488 nm. Little non-specific signal is observed (partial sedimentation of the nanoparticles) whereas the specific signal is significantly more intense and dependent on the concentration.

Example 4

In Vivo Cell Labelling

The QDots-cyclooctynes synthesized as described in Example 1 are used to carry out cell labelling. The purpose is to image the metabolic incorporation of sialic acids modified by azides in the membrane surfaces of CHO cells in culture.

Figure 2:
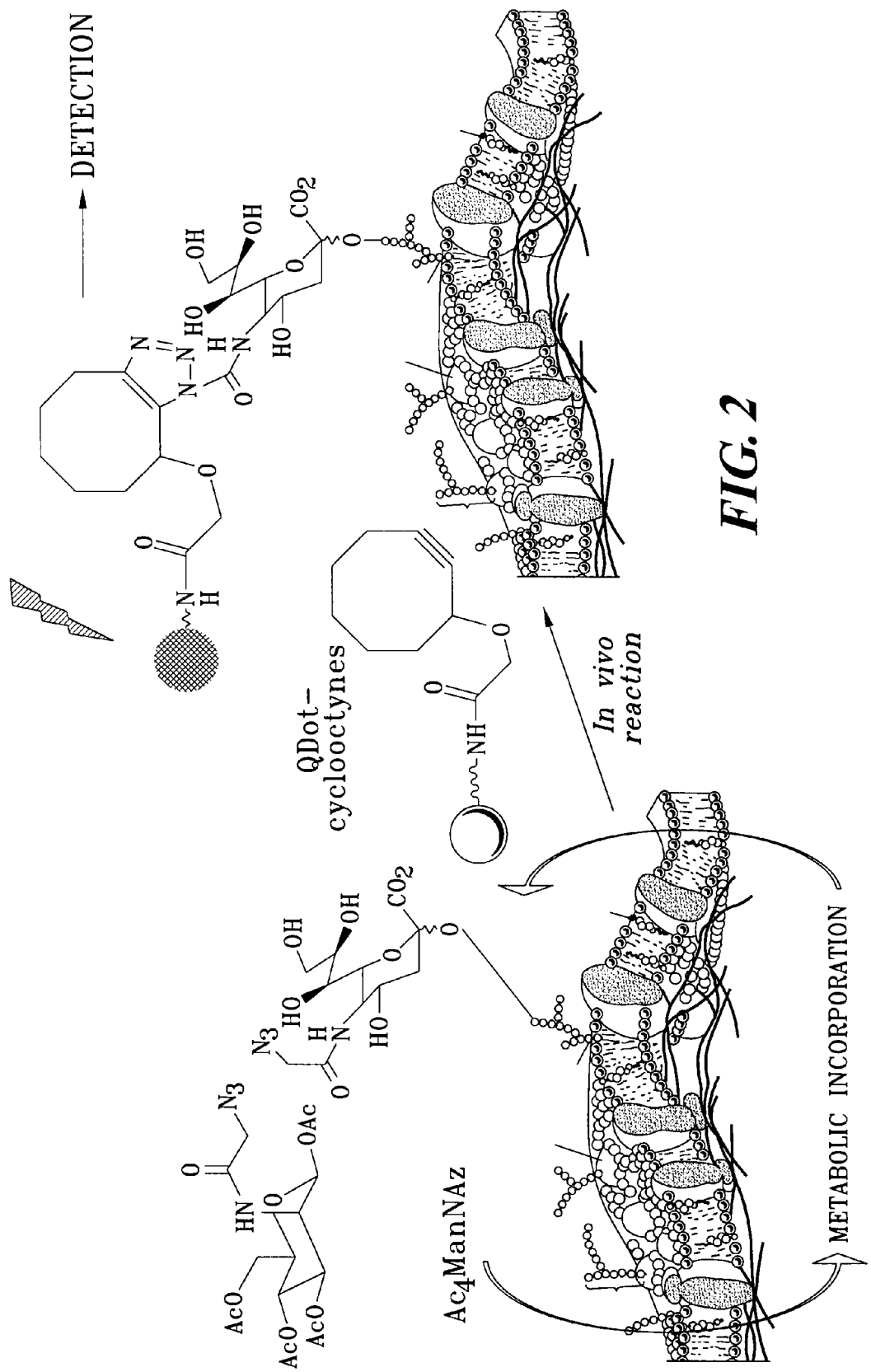
FIG. 2: It illustrates the principle of the metabolic incorporation of $Ac_4ManNAz$ and its conversion to sialic acid bearing the $N_3$, group, which is then incorporated into the proteoglycans expressed on the cellular membranes and enables labelling in a second step via a click reaction with the QDots-cyclooctynes.

FIG. 2 illustrates the principle of the metabolic incorporation of Ac$_4$ManNAz and its conversion to sialic acid bearing the N$_3$ group, which is then incorporated into the proteoglycans expressed on the cell membranes and enables the labelling, in a second step, via a click reaction with the QDots-cyclooctynes.

The incorporation of an azide-modified mannosamine (Ac$_4$ManNAz) over 3 days is then displayed by incubating for 4 h at 4° C. with the QDot-cyclooctynes probe, then observed by fluorescence microscopy.

A negative control is obtained by the identical incorporation of a mannosamine that does not bear the azide modification (Ac$_4$ManNAc). The nuclei of the cells have been labelled by DAPI. A very clear labelling of the membranes is visible in the case of the incubation with the Qdot-cyclooctynes that makes it possible to validate the use of such objects for imaging.

The invention claimed is:

1. A method for surface-modifying a semiconductor nanocrystal, comprising:
    providing a semiconductor nanocrystal comprising an organic coating layer at an outer surface of the nanocrystal, the organic coating comprising at least one reactive group G1 that reacts according to a click chemistry cycloaddition reaction;
    providing an adjoining material comprising at least one G2 group at a surface of the adjoining material, the G2 group being complementary to the G1 group in the click chemistry cycloaddition reaction; and
    bringing the nanocrystal together with the adjoining material under conditions favorable to the interaction of the G1 group and the G2 group;
    wherein:
    the G1 group is an azide and the G2 group is a strained cycloalkynyl radical, or the G2 group is an azide and the G1 group is a strained cycloalkynyl radical; and
    the organic coating layer of the semiconductor nanocrystal comprises at least one specific ligand given by the general formula (I):

L-X-E-A-G1        (I)

in which:
    L is a chelating ligand selected from the group consisting of phosphine, phosphine oxides, fatty chains having an end amine, fatty chains having an end carboxylic acid, fatty chains having an end thiol functional group, a 1,1-dithiolate group, and a 1,1-diselenoate group;
    E is an organic spacer group given by the general formula (II):

—R$_1$—R—        (II)

where
    R$_1$ represents:
        a single bond;
        a group

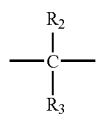

where R$_2$ and R$_3$ independently represent a hydrogen, an alkyl radical, an aryl radical, an alkoxy radical, a halogen;
a group

where R' represents a hydrogen, an alkyl radical, an aryl radical, an alkoxy radical, or a halogen;
a group

where R' represents a hydrogen, an alkyl radical, an aryl radical, an alkoxy radical, or a halogen;
a group

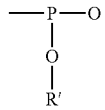

where R' represents a hydrogen, an alkyl radical, an aryl radical, an alkoxy radical, or a halogen;
—O—;
—S—; or
—Se—; and
R represents:
    a linear or branched alkylene group having from 1 to 30 carbon atoms, one or more carbon atoms of the alkylene group optionally being replaced by one or more heteroatoms chosen from O, N, S, P and Si, the alkylene group optionally further comprising one or more double and/or triple bonds, and the alkylene group optionally being further substituted by one or more groups chosen from halogens, heterocycles, aryl groups, hydroxyl groups, alkoxy groups, amino groups, acryl groups, carboxamido groups, =O, —CHO, —CO$_2$H, —SO$_3$H, —PO$_3$H$_2$, —PO$_4$H$_2$, —NHSO$_3$H, sulphonamide groups, monoalkylamino groups, trialkylammonium radicals, or dialkyl(C$_1$-C$_4$)amino radicals in which two alkyl groups optionally form a ring together with the nitrogen atom of the dialkylamino group to which they are bonded, the ring being optionally interrupted by one or more nitrogen, oxygen, or sulfur atoms; or
    a heterocycle, an aryl radical, an aryl radical fused to one or more other aryl rings and/or alkyl rings or heterocycles, a cycloalkyl radical, a cycloalkyl-alkyl radical, an alkyl-cycloalkyl radical, an arylalkyl radical, an alkylaryl radical, a heterocycloalkyl radical, or an alkyl-heterocycloalkyl radical;
X represents a reaction product of one reactive functional group present on the chelating ligand L and a complementary reactive functional group present on the organic spacer group E;
A represents a single bond or a group chosen from the group consisting of —CONH, —NHCO—, —OCH$_2$CONH—, —NHCOCH$_2$O—, —O— and —S—; and
G1 represents a strained cycloalkynyl or azide radical.

2. The method of claim 1, wherein the G1 group is a strained cycloalkynyl radical.

3. The method of claim 1, wherein the strained cycloalkynyl radical is a cyclooctynyl radical.

4. The method of claim 1, wherein:
the semiconductor nanocrystal has a core/shell structure;
the core comprises a nanocrystal comprising at least one of a metal and a semiconductor compound; and
the shell comprises at least one of a layer of a metal and a layer of a semiconductor compound comprising a metal.

5. The method of claim 4, wherein:
the core comprises a first semiconductor compound A(II)B(VI), in which A represents a metal or a metalloid in the +II oxidation state and B represents an element in the −II oxidation state, or a C(III) D(V) compound in which C represents a metal or a metalloid in the +III oxidation state and D represents an element in the −III oxidation state; and
the shell comprises a second semiconductor compound A(II)B(VI) different from the first semiconductor compound, the second semiconductor compound being selected from the group consisting of ZnSe, ZnS and CdS.

6. The method of claim 1, wherein bringing the nanocrystal together with the adjoining material comprises bringing the nanocrystal together with the adjoining material at ambient temperature in an aqueous medium.

7. The method of claim 1, wherein the adjoining material comprises a substrate selected from the group consisting of metallic substrates, semiconductor substrates, oxide substrates, and organic substrates.

8. The method of claim 1, wherein the adjoining material comprises a molecule of interest.

9. The method of claim 8, wherein the molecule of interest comprises at least one member selected from the group consisting of markers, dyes, fluorophores, linkers, therapeutic, cosmetic or phytosanitary active agents, members of a specific binding pair, peptides, amino acids, and amino acid residues, polypeptides, sugars and sugar residues, photosensitizers, porphyrins and compounds that have cis-trans isomerism.

10. A surface-modified semiconductor nanocrystal obtained by the method of claim 1.

* * * * *